United States Patent
Kumano et al.

(10) Patent No.: US 9,835,635 B2
(45) Date of Patent: Dec. 5, 2017

(54) METHOD FOR MEASURING CLOTTING TIME, METHOD FOR DETERMINING PRESENCE OR ABSENCE OF LUPUS ANTICOAGULANT, AND REAGENT KIT FOR DETECTING LUPUS ANTICOAGULANT

(71) Applicants: SCHOOL JURIDICAL PERSON HIGASHI-NIPPON-GAKUEN, Ishikari-gun, Hokkaido (JP); SYSMEX CORPORATION, Kobe-shi, Hyogo (JP)

(72) Inventors: Osamu Kumano, Kobe (JP); Haruki Yamaguchi, Kobe (JP); Takeshi Suzuki, Kobe (JP); Masahiro Ieko, Ishikari-gun (JP)

(73) Assignees: SCHOOL JURIDICAL PERSON HIGASHI-NIPPON-GAKUEN, Hokkaido (JP); SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 15/082,005

(22) Filed: Mar. 28, 2016

(65) Prior Publication Data
US 2016/0291041 A1   Oct. 6, 2016

(30) Foreign Application Priority Data
Mar. 31, 2015  (JP) ................................. 2015-073603

(51) Int. Cl.
| | | |
|---|---|---|
| G01N 33/86 | (2006.01) | |
| G01N 33/68 | (2006.01) | |
| G01N 33/49 | (2006.01) | |
| G01N 33/564 | (2006.01) | |
| G01N 33/92 | (2006.01) | |
| G01N 33/20 | (2006.01) | |

(52) U.S. Cl.
CPC ......... *G01N 33/86* (2013.01); *G01N 33/4905* (2013.01); *G01N 33/564* (2013.01); *G01N 33/6854* (2013.01); *G01N 33/20* (2013.01); *G01N 33/92* (2013.01); *G01N 2800/224* (2013.01)

(58) Field of Classification Search
CPC .... G01N 33/48; G01N 33/49; G01N 33/4905; G01N 33/86; G01N 33/92; G01N 2015/0065; G01N 2333/745; G01N 2333/96463; G01N 33/6854; G01N 33/564; G01N 33/20; G01N 2800/224
USPC .............. 436/63, 69, 71, 79, 80, 81; 435/13; 422/430, 73; 73/64.41; 600/369
See application file for complete search history.

(56) References Cited

U.S. PATENT DOCUMENTS

| | | | | |
|---|---|---|---|---|
| 5,451,509 | A * | 9/1995 | Speck .................... | A61K 33/24 435/13 |
| 5,705,198 | A * | 1/1998 | Triplett .................. | C07K 14/46 424/542 |
| 2003/0104493 | A1* | 6/2003 | Ortel ...................... | G01N 21/77 435/7.9 |
| 2009/0061468 | A1* | 3/2009 | Hoshiko ................ | G01N 33/86 435/13 |
| 2012/0052585 | A1 | 3/2012 | Okuda et al. | |
| 2012/0220038 | A1* | 8/2012 | Okuda .................. | G01N 33/564 436/69 |
| 2014/0127725 | A1* | 5/2014 | Ieko ........................ | C12Q 1/56 435/13 |
| 2014/0127726 | A1* | 5/2014 | Ieko ........................ | C12Q 1/56 435/13 |

FOREIGN PATENT DOCUMENTS

WO        90/11368 A1    10/1990

OTHER PUBLICATIONS

Kumano et al. Journal of Thrombosis and Haemostasis, vol. 11, 2013, pp. 1919-1922.*
Kumano et al. Thrombosis Research, vol. 134, May 29, 2014, pp. 503-509.*

* cited by examiner

*Primary Examiner* — Maureen Wallenhorst
(74) *Attorney, Agent, or Firm* — Sughrue Mion, PLLC (57) ABSTRACT

Disclosed is a method for measuring clotting time including: preparing a measurement sample by mixing a blood specimen suspected to contain a lupus anticoagulant, an activator, and a divalent-metal-ion-producing compound for facilitating formation of a phospholipid-containing complex; and measuring a clotting time after adding, to the measurement sample, an aqueous solution of a calcium salt as a coagulation initiator.

20 Claims, 4 Drawing Sheets

METHOD FOR MEASURING CLOTTING TIME, METHOD FOR DETERMINING PRESENCE OR ABSENCE OF LUPUS ANTICOAGULANT, AND REAGENT KIT FOR DETECTING LUPUS ANTICOAGULANT

CROSS REFERENCE TO RELATED APPLICATIONS

This application claims priority from prior Japanese Patent Application No. 2015-073603, filed on Mar. 31, 2015, entitled "Method for measuring clotting time, method for determining presence or absence of lupus anticoagulant, and reagent kit for detecting lupus anticoagulant", the entire content of which is incorporated herein by reference.

FIELD OF THE INVENTION

The present invention relates to a method for measuring clotting time. The present invention also relates to a method for determining the presence or absence of a lupus anticoagulant, and relates to a reagent kit for detecting a lupus anticoagulant.

BACKGROUND

Antiphospholipid syndrome is a general term for a group of diseases for which antiphospholipid antibodies are observed in blood and which present clinical symptoms such as arteriovenous thrombosis and recurrent abortion and fetal death. "Antiphospholipid antibodies" (aPL) is a general term for autoantibodies which bind to phospholipids or to complexes of phospholipids and proteins. There are various antibodies as aPL, and examples thereof are anti-cardiolipin antibodies, anti-β2 glycoprotein I antibodies, phosphatidyl-serine-dependent antiprothrombin antibodies, and lupus anticoagulants (LA).

LA is defined as "an immunoglobulin that inhibits phospholipid-dependent blood coagulation reactions without inhibiting individual coagulation factor activities". LA is considered as an autoantibody that inhibits phospholipids in phospholipid-dependent coagulation reactions. On the other hand, although LA inhibits phospholipids necessary for phospholipid-dependent coagulation reactions, patients having LA show thrombotic symptoms.

Currently, LA screening tests utilize a method in which a reagent containing a low concentration of a phospholipid is used to facilitate phospholipid-inhibiting reaction caused by LA, thereby to confirm prolongation of clotting time. In such tests, a reagent for measuring activated partial thromboplastin time (APTT) is diluted to be used, or a reagent whose phospholipid concentration is set to be low in advance, such as in PTT-LA (registered trademark) (Roche Diagnostics), is used.

U.S. Patent Application Publication No. 2012/0052585 discloses a reagent kit that is specialized in detecting LA and that includes two types of reagents having different phospholipid concentrations. This reagent kit suppresses prolongation of clotting time caused by LA, thereby enabling a group of LA positive specimens to be clearly distinguished from a group of the other specimens. However, detection of LA by this reagent kit requires measurement of clotting time for each of the two types of reagents.

Conventional APTT measuring reagents used in screening tests do not have satisfactory sensitivities to LA. Therefore, with conventional reagents, even in mixing tests with normal plasma, it is difficult to clearly distinguish the group of LA positive specimens from the group of the other specimens. Thus, there is a demand for means that can improve sensitivity to LA and that can accurately distinguish the group of LA positive specimens from the group of the other specimens.

SUMMARY OF THE INVENTION

The scope of the present invention is defined solely by the appended claims, and is not affected to any degree by the statements within this summary.

DETAILED DESCRIPTION OF THE PREFERRED EMBODIMENTS

[1. Method for Measuring Clotting Time]

In a method for measuring clotting time (hereinafter, also simply referred to as "measurement method") according to the present embodiment, a blood specimen suspected to contain LA, an activator, and a compound that produces divalent metal ions (hereinafter, referred to as divalent-metal-ion-producing compound) are mixed to prepare a measurement sample.

In the present embodiment, the blood specimen suspected to contain LA is not particularly limited as long as it is a blood specimen suspected to have a cause of prolongation of clotting time. Examples of such a blood specimen include a specimen for which prolongation of clotting time has been observed in an ordinary coagulation test, and a group of specimens obtained from a plurality of subjects including individuals suspected to have causes of prolongation of clotting time. Examples of such causes of prolongation of clotting time include, in addition to LA, coagulation factor inhibitors, coagulation factor deficiencies, and drugs that act on blood coagulation such as heparin.

As the kind of the blood specimen, plasma is preferable, and a plasma having platelets removed therefrom is preferable in particular. Platelets can be removed by a known technique such as centrifugation or filtration. In the present embodiment, a plasma prepared from blood obtained from a subject can be used (hereinafter, plasma derived from a subject will also be referred to as "subject plasma"). As control specimens, a commercially available LA-containing plasma, a coagulation-factor-inhibitor-containing plasma, a coagulation-factor-deficient plasma, a heparin-added plasma, and the like may further be measured.

In the present embodiment, a normal blood specimen may be further measured. An example of the normal blood specimen is a plasma prepared from blood of a healthy individual, or a commercially available normal plasma. An example of the commercially available normal plasma is CRYOcheck Pooled Normal Plasma (Precision BioLogic Inc.).

When the method of the present embodiment is used in a cross mixing test, a specimen obtained by mixing a subject plasma and a normal plasma with at least one mixing ratio (hereinafter, also referred to as "mixed plasma") is used. The mixing ratio between the subject plasma and the normal plasma can be determined as appropriate in accordance with the amount of the subject plasma, the kind of quantification index described later, or the like. As the proportion of the subject plasma in the mixed plasma, at least one is selected from among, for example, 5, 10, 15, 20, 25, 30, 35, 40, 45, 50, 55, 60, 65, 70, 75, 80, 85, 90, and 95%(v/v). Among these, it is preferable to prepare a mixed specimen in which the proportion of the subject plasma is 50%(v/v).

The divalent-metal-ion-producing compound is not particularly limited as long as the compound produces divalent metal ions in an appropriate solvent and anions produced from the compound do not inhibit blood coagulation reaction. Examples of such a compound include salts composed of divalent metals, and inorganic acids or organic acids. Among these, salts composed of divalent metals and inorganic acids are preferable, and examples of such salts include salts composed of divalent metals and an acid such as hydrochloric acid, sulfuric acid, or nitric acid. Examples of more preferable divalent metal salts include a salt of at least one metal selected from calcium, magnesium, zinc, and copper. The divalent-metal-ion-producing compound may be an anhydride or a hydrate. In the present embodiment, it is preferable that the divalent-metal-ion-producing compound is used in the form of a solution in which the compound is dissolved with an appropriate solvent, in particular in the form of an aqueous solution.

In this technology, it is known that LA binds to a complex of phospholipids and calcium ions, or to a complex of phospholipids, calcium ions, and proteins, thereby inhibiting coagulation reaction. Thus, in the measurement method according to the present embodiment, it is intended that by adding the divalent-metal-ion-producing compound, a complex of phospholipids and the divalent metal ions, or a complex of phospholipids, the divalent metal ions, and proteins (hereinafter, these complexes will be also referred to as "phospholipid-containing complex") is formed in advance, to the extent that coagulation is not caused. That is, in the measurement method according to the present embodiment, the divalent-metal-ion-producing compound is added to the blood specimen in order to facilitate formation of the phospholipid-containing complex. By forming in advance a complex to be bound by LA, it is expected that coagulation inhibiting reaction by LA easily occurs. Thus, it is considered that if LA is contained in the blood specimen, the measurement method according to the present embodiment shows improved sensitivity to LA compared with that of an ordinary clotting time measurement method. It should be noted that the phospholipid in the complex may be an endogenous phospholipid contained in the blood specimen, an added phospholipid described later, or both of them.

The step of preparing the measurement sample is not intended to cause coagulation (i.e., to produce fibrin) by adding the divalent-metal-ion-producing compound. Therefore, it is preferable that the final concentration of the divalent-metal-ion-producing compound in the measurement sample is lower than the final concentration of a calcium salt added in the step of measuring clotting time described later. In the present embodiment, the final concentration of the divalent-metal-ion-producing compound is, for example, not lower than 0.01 mM and lower than 2 mM, and preferably, not lower than 0.2 mM and not higher than 1.5 mM.

The activator is not particularly limited as long as the activator is a known substance that is acknowledged to facilitate blood coagulation in vitro. Such an activator is preferably a contact factor activator, and specifically, an example of the activator is a substance having negative charge. Examples of such a substance include ellagic acid, kaolin, cerite, and silica. As the ellagic acid, ellagic acid forming a chelate with a metal ion may be added.

The final concentration of the activator in the measurement sample is not particularly limited, and may be substantially the same as that in a conventional clotting time measurement method. In this technology, for example, in the case with ellagic acid, it is known that the final concentration of the activator in the measurement sample is usually not lower than 3.5 μM and not higher than 150 μM, and preferably, not lower than 10 μM and not higher than 50 μM. In the case with silica, it is known that the final concentration of the activator is usually not lower than 0.04 mg/ml and not higher than 0.4 mg/ml, and preferably, not lower than 0.07 mg/ml and not higher than 0.2 mg/ml.

In the present embodiment, in order to facilitate blood coagulation, the phospholipid may be further added during the preparation of the measurement sample. Examples of the phospholipid include phosphatidylethanolamine (PE), phosphatidylcholine (PC), and phosphatidylserine (PS). In the present embodiment, one, preferably two, or further preferably all phospholipids selected from PE, PC, and PS may be added. The phospholipid may be a naturally occurring phospholipid or a synthetic phospholipid. Among those, from the viewpoint of improving LA detection sensitivity, a synthetic phospholipid or a natural phospholipid purified to have a purity of 99% is preferable. Fatty acid side chains of PE, PC, and PS are not particularly limited, but examples thereof include palmitic acid, oleic acid, and stearic acid. Among these, oleic acid is preferable.

The final concentration of the phospholipid in the measurement sample is not particularly limited, but is, for example, not lower than 1 μg/ml and not higher than 150 μg/ml, and preferably not lower than 5 μg/ml and not higher than 50 μg/ml. When PE, PC, and PS are contained as the phospholipid, the final concentration of PE in the measurement sample is, for example, not lower than 1 μg/ml and not higher than 50 μg/ml, and preferably not lower than 5 μg/ml and not higher than 25 μg/ml; the final concentration of PC is, for example, not lower than 1 μg/ml and not higher than 100 μg/ml, and preferably not lower than 5 μg/ml and not higher than 80 μg/ml; and the final concentration of PS is, for example, not lower than 0.1 μg/ml and not higher than 50 μg/ml, and preferably not lower than 1 μg/ml and not higher than 10 μg/ml.

In the present embodiment, the clotting time may be any clotting time that is measured on the basis of a known measurement principle in this technology. Examples of such clotting time include activated partial thromboplastin time (APTT), dilute activated partial thromboplastin time (dAPTT), kaolin clotting time (KCT), dilute Russell viper venom clotting time (dRVVT), thrombin time (TT), and dilute thrombin time (dTT). Among these, APTT and dAPTT are preferable.

In the present embodiment, when kaolin is used as the activator and the clotting time is measured on the basis of the KCT measurement principle, an endogenous phospholipid contained in the blood specimen is used in coagulation reaction. Thus, in this case, it is not necessary to add the above-described phospholipid during preparation of the measurement sample.

In the present embodiment, when the clotting time is measured on the basis of the dRVVT measurement principle, a snake venom may further be added during preparation of the measurement sample. Examples of the snake venom include Russell viper venom, textarin venom, and ecarin venom.

Hereinafter, the activator, the phospholipid, the snake venom are also collectively referred to as "component necessary for coagulation". In the present embodiment, the order of mixing the blood specimen, the divalent-metal-ion-producing compound, and the component necessary for coagulation is not particularly limited. For example, after mixing the blood specimen and the divalent-metal-ion-producing compound, the component necessary for coagulation may be mixed. Alternatively, after mixing the blood specimen and the component necessary for coagulation, the divalent-metal-ion-producing compound may be mixed. Alternatively, after mixing the divalent-metal-ion-producing compound and the component necessary for coagulation, the blood specimen may be mixed. Still alternatively, the blood specimen, the divalent-metal-ion-producing compound, and the component necessary for coagulation may be mixed substantially at the same time. It should be noted that when mixing the blood specimen and the component necessary for coagulation first, it is preferable that the blood specimen and the component necessary for coagulation are incubated under a predetermined condition, and then the divalent-metal-ion-producing compound is mixed. Such a predetermined condition may be any known condition that facilitates reaction between the coagulation factor in the blood specimen and the component necessary for coagulation. An example of the predetermined condition is performing the incubation at a temperature of not lower than 35° C. and not higher than 40° C., for a time period of not shorter than 2 minutes and not longer than 5 minutes.

In the measurement method according to the present embodiment, an aqueous solution of the calcium salt as a coagulation initiator is added to the measurement sample prepared as described above, and clotting time is measured. Thus, the clotting time is measured, with the time point of the addition and mixing of the aqueous solution of the calcium salt defined as the measurement start point.

The calcium salt is not particularly limited as long as it produces calcium ions in the measurement sample. An example of the calcium salt is calcium chloride. The final concentration of the calcium salt in the measurement sample after addition of the aqueous solution of the calcium salt may be any concentration that is sufficient to cause coagulation, and is, for example, not lower than 2 mM and not higher than 20 mM, and preferably not lower than 4 mM and not higher than 10 mM.

In the present embodiment, when LA is contained in the blood specimen, in order to facilitate reaction between LA and the above-described phospholipid-containing complex in the measurement sample, it is preferable that the measurement sample is incubated under a predetermined condition, and then the aqueous solution of the calcium salt is added thereto. An example of such a condition is performing the incubation at a temperature of not lower than 35° C. and not higher than 40° C., for a time period of not shorter than 2 minutes and not longer than 5 minutes.

In the present embodiment, preparation of the measurement sample and measurement of the clotting time may be performed manually or by a fully automatic clotting time measurement apparatus, but is preferably performed by a fully automatic clotting time measurement apparatus. Examples of such a fully automatic clotting time measurement apparatus include CS-5100 (Sysmex Corporation), CS-2400 (Sysmex Corporation), and CS-2000i (Sysmex Corporation).

With respect to the measurement method according to the present embodiment, as described above, it is considered that by adding the divalent-metal-ion-producing compound, the above-described phospholipid-containing complex is formed in advance, and thus, sensitivity to LA has been improved. Actually, as shown in Example 1 described later, when LA is contained in the blood specimen, the clotting time tends to be more prolonged, compared with that by an ordinary clotting time measurement method. On the other hand, since the effect by the compound is selective to LA, there is little or substantially no influence on the clotting time of blood specimens having clotting prolongation causes of clotting disorder, other than LA (for example, coagulation factor deficient specimens, heparin-containing specimens, etc.).

[2. Method for Determining the Presence or Absence of LA]

In the present embodiment, whether a blood specimen contains LA can be determined on the basis of clotting time obtained by the measurement method described above. Hereinafter, a method for determining the presence or absence of LA will be described.

In the method for determining the presence or absence of LA according to the present embodiment, the step of preparing a measurement sample and the step of measuring clotting time are the same as described with regard to the measurement method above. In the present embodiment, the blood specimen is not particularly limited, and may be any blood specimen that is derived from a subject. In addition, as control specimens, various types of commercially available plasmas containing a cause of prolongation of clotting time and commercially available normal plasmas may be used.

In the present embodiment, when LA is contained in a blood specimen, the clotting time tends to be more prolonged by adding the divalent-metal-ion-producing compound as mentioned above. On the other hand, the effect by the compound is selective to LA. Thus, in the present embodiment, when the measured clotting time is longer than a predetermined clotting time, it may be determined that the blood specimen contains LA. In contrast, when the measured clotting time is shorter than or equal to the predetermined clotting time, it may be determined that the blood specimen does not contain LA. As the predetermined clotting time, the clotting time of normal plasma is preferable. The clotting time of normal plasma may be a clotting time that has been actually measured in a similar manner with the subject plasma, or may be a clotting time that is known as a normal value or a reference value in the measurement principle for the clotting time measuring reagent to be used.

In a preferable embodiment, a quantification index is obtained on the basis of the measured clotting time, and then, whether the specimen contains LA is determined on the basis of the value of the obtained quantification index. For example, the value of the quantification index is compared with a predetermined threshold value, and when the value of the quantification index is greater than or equal to the predetermined threshold value, it is possible to determine that the blood specimen contains LA. In contrast, when the value of the quantification index is smaller than the predetermined threshold value, it is possible to determine that the blood specimen does not contain LA.

In the present embodiment, the quantification index is not particularly limited as long as it is an index for quantitatively evaluating the result of a cross mixing test on the basis of the clotting time of a subject plasma, a normal plasma and/or a mixed plasma thereof. A known quantification index may be used. Examples of the known quantification index include Index of Circulating Anticoagulant (ICA), Percent Correction (PC), and Response Curve-Score (RC-S). Among these, ICA is preferable. ICA is disclosed by Pengo V. et al., in "Update of the guidelines for lupus anticoagulant detection", Journal of Thrombosis and Haemostasis 2009; 7: 1737-1740. PC is disclosed by Chang S-H. et al., in "'Percent Correction' Formula for Evaluation of Mixing Studies", Am J Clin Pathol 2002; 117: 62-73. RC-S is disclosed by Sumiyoshi Naito et al., in "Kousakongou shiken no aratana hantei houhou niyoru LA kenshutsu no hyouka to yuuyousei (Evaluation and usefulness of LA detection by new determination method for cross mixing test: provisional translation)", Rinsho Byori, 2012, vol. 60 Supplement, page 166.

ICA is also referred to as Rosner Index, and is an index that is used in determination of LA specimens. ICA is calculated by the formula below:

$$ICA=[(D-A)/G]\times 100$$

(wherein, A: clotting time of normal plasma, D: clotting time of mixed plasma in which proportion of subject plasma is 50% (v/v), G: clotting time of subject plasma.).

In the case with PC, the calculation formula differs depending on the proportion of subject plasma in mixed plasma, as shown below:

$$PC(9:1)=[(G-B)/(G-A)]\times 100$$

$$PC(8:2)=[(G-C)/(G-A)]\times 100$$

$$PC(5:5)=[(G-D)/(G-A)]\times 100$$

$$PC(2:8)=[(G-E)/(G-A)]\times 100$$

$$PC(1:9)=[(G-F)/(G-A)]\times 100$$

(wherein, A: clotting time of normal plasma, B: clotting time of mixed plasma in which proportion of subject plasma is 10% (v/v), C: clotting time of mixed plasma in which proportion of subject plasma is 20% (v/v), D: clotting time of mixed plasma in which proportion of subject plasma is 50% (v/v), E: clotting time of mixed plasma in which proportion of subject plasma is 80% (v/v), F: clotting time of mixed plasma in which proportion of subject plasma is 90% (v/v), G: clotting time of subject plasma.).

RC-S is an index to which Rosner Index has been applied and is calculated in the following manner. First, scores of mixed plasmas in which the proportions of the subject plasma are respectively 20% (v/v) and 50% (v/v) are calculated by the following formulae:

$$RC\text{-}S(20)=[(C-B)/D]\times 100$$

$$RC\text{-}S(50)=[(D-C)/E]\times 100$$

(wherein, B: clotting time of mixed plasma in which proportion of subject plasma is 10% (v/v), C: clotting time of mixed plasma in which proportion of subject plasma is 20% (v/v), D: clotting time of mixed plasma in which proportion of subject plasma is 50% (v/v), E: clotting time of mixed plasma in which proportion of subject plasma is 80% (v/v).).

Next, with respect to the mixed plasmas in which the proportions of the subject plasma are respectively 20% (v/v) and 50% (v/v), control scores are calculated by the following formulae on the assumption that the reaction curve of the cross mixing test is a straight line:

$$RC\text{-}Sc(20)=[[(3\times B+D)/4-B]/D]\times 100$$

$$RC\text{-}Sc(50)=[[(C+E)/2-B]/E]\times 100$$

(wherein, B: clotting time of mixed plasma in which proportion of subject plasma is 10% (v/v), C: clotting time of mixed plasma in which proportion of subject plasma is 20% (v/v), D: clotting time of mixed plasma in which proportion of subject plasma is 50% (v/v), E: clotting time of mixed plasma in which proportion of subject plasma is 80% (v/v).).

Then, with respect to each of the mixed plasmas in which the proportions of the subject plasma are respectively 20% (v/v) and 50% (v/v), the proportion of the score (S) to the control score (Sc) is calculated, and the sum of the two calculated proportions is defined as the quantification index (see formula below).

$$S/Sc(20+50)=(RC\text{-}S(20)/RC\text{-}Sc(20))\times 100+(RC\text{-}S(50)/RC\text{-}Sc(50))\times 100$$

In the present embodiment, the predetermined threshold value is not particularly limited. For example, through accumulation of data regarding LA positive specimens, and data regarding specimens having causes of prolongation of clotting time other than LA, such as coagulation factor deficiency, a predetermined threshold value can be empirically set. Alternatively, with respect to each of a group of LA positive specimens and a group of specimens having causes of prolongation of clotting time other than LA, clotting time may be measured to obtain a value of the quantification index, and then, on the basis of the obtained value, a value that can clearly distinguish the groups from each other may be set as the predetermined threshold value. For calculation of the predetermined threshold value, a statistical technique such as ROC analysis may be used.

[3. Reagent Kit for Detecting LA]

Figure 3:
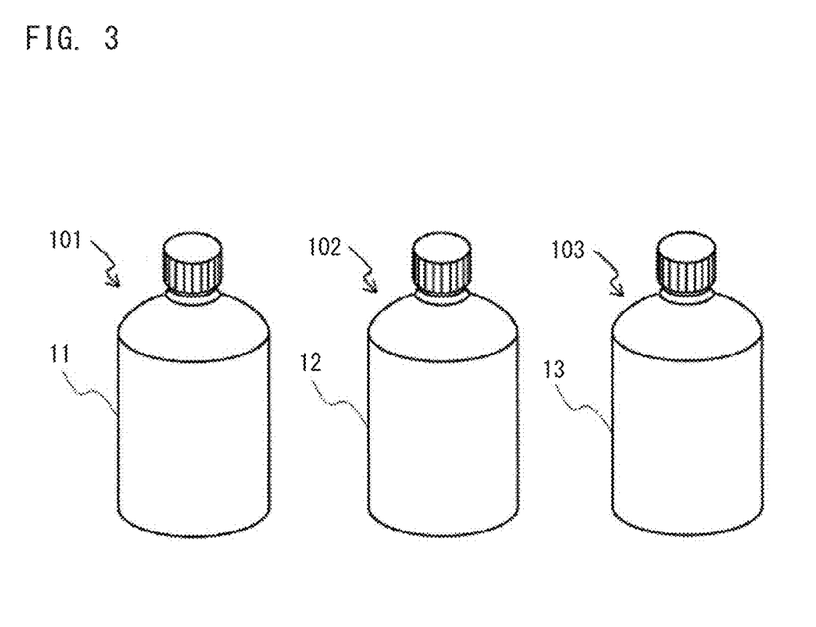
FIG. 3 shows one example of a reagent kit according to the present embodiment.

The scope of the present disclosure also includes a reagent kit for detecting LA. The reagent kit according to the present embodiment includes: a first reagent containing the divalent-metal-ion-producing compound for facilitating formation of the phospholipid-containing complex; a second reagent containing the activator; and a coagulation initiation reagent composed of the aqueous solution of the calcium salt. FIG. 3 shows one example of a reagent kit according to the present embodiment, the reagent kit including: a first reagent 101 contained in a first container 11; a second reagent 102 contained in a second container 12; and a coagulation initiation reagent 103 contained in a third container 13.

In the present embodiment, at least one of the first reagent and the second reagent may further contain a phospholipid. The concentration of the phospholipid in the reagent is not particularly limited, but is, for example, not lower than 30 µg/ml and not higher than 400 µg/ml, and preferably not lower than 10 µg/ml and not higher than 100 µg/ml. When PE, PC, and PS are contained as the phospholipid, the PE concentration in the reagent is, for example, not lower than 10 µg/ml and not higher than 100 µg/ml, and preferably not lower than 20 µg/ml and not higher than 50 µg/ml; the PC concentration is, for example, not lower than 10 µg/ml and not higher than 300 µg/ml, and preferably not lower than 10 µg/ml and not higher than 100 µg/ml; and the PS concentration is, for example, not lower than 1 µg/ml and not higher than 75 µg/ml, and preferably not lower than 2 µg/ml and not higher than 15 µg/ml. When both of the first reagent and the second reagent contain the phospholipid, it is preferable that the total of the phospholipid concentrations of the respective reagents is within the above ranges.

Here, the kinds of the divalent-metal-ion-producing compound, the activator, the phospholipid and the aqueous solution of the calcium salt are the same as those described with regard to the measurement method above.

In the present embodiment, the concentration of the divalent-metal-ion-producing compound in the first reagent is not particularly limited as long as the final concentration thereof in the measurement sample can be adjusted within the ranges shown above. When clotting time is measured by a fully automatic clotting time measurement apparatus, the concentration of the divalent-metal-ion-producing compound in the first reagent is, for example, not lower than 0.1 mM and not higher than 20 mM, and preferably not lower than 1.0 mM and not higher than 10 mM, in consideration of the reagent amount that the apparatus can aspirate.

In the present embodiment, the concentration of the activator in the second reagent is not particularly limited as long as the final concentration thereof in the measurement sample can be adjusted within the ranges shown above. When clotting time is measured by a fully automatic clotting time measurement apparatus, the concentration of the activator in the second reagent is, for example, in the case with ellagic acid, not lower than 10 µM and not higher than 400 µM, and preferably not lower than 50 µM and not higher than 150 µM, in consideration of the reagent amount that the apparatus can aspirate. In the case with silica, it is known that the concentration of the activator is usually not lower than 0.1 mg/ml and not higher than 1.0 mg/ml, and preferably not lower than 0.2 mg/ml and not higher than 0.6 mg/ml.

The concentration of the calcium salt in the coagulation initiation reagent composed of the aqueous solution of the calcium salt is not particularly limited as long as the concentration can be adjusted to a final concentration that can cause coagulation to occur. When clotting time is measured by a fully automatic clotting time measurement apparatus, the concentration of the calcium salt in this reagent is, for example, not lower than 2.5 mM and not higher than 40 mM, and preferably not lower than 10 mM and not higher than 30 mM, in consideration of the reagent amount that the apparatus can aspirate.

Figure 4:
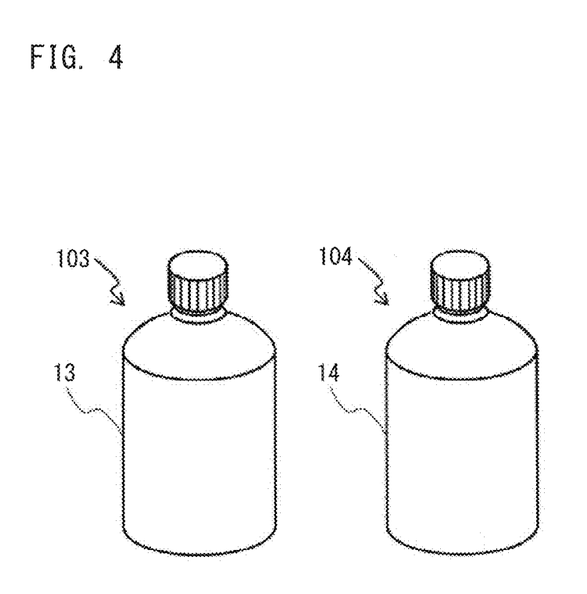
FIG. 4 shows one example of a reagent kit according to the present embodiment.

A reagent kit according to another embodiment includes: a first reagent that contains the activator and the divalent-metal-ion-producing compound for facilitating formation of the phospholipid-containing complex; and the coagulation initiation reagent composed of the aqueous solution of the calcium salt. FIG. 4 shows one example of a reagent kit according to the present embodiment, the reagent kit including: a first reagent 104 contained in a fourth container 14; and the coagulation initiation reagent 103 contained in the third container 13. The first reagent may further contain the phospholipid.

As described above, in the present embodiment, when LA is contained in the blood specimen, the clotting time tends to be more prolonged by adding the divalent-metal-ion-producing compound. On the other hand, the effect by the compound is selective to LA. Thus, the reagent kit according to the present embodiment is suitable for screening tests and mixing tests for detecting LA. The usage procedure of the reagent kit according to the present embodiment is the same as that described with regard to the clotting time measurement method and the method for determining the presence or absence of LA described above.

Hereinafter, the present disclosure will be described in detail with reference to Examples. However, the present disclosure is not limited to these Examples.

EXAMPLE

Example 1

With respect to various types of blood specimens including LA positive specimens, clotting time was measured by the measurement method according to the present embodiment and by a conventional measurement method, and the measurement results were compared.

(1) Reagent

As the reagent containing the activator and the phospholipid, PTT-LA (registered trademark)(Roche Diagnostics) was used (hereinafter, this reagent will be referred to as "APTT reagent"). As the aqueous solution of the calcium salt serving as the coagulation initiator, a 25 mM calcium chloride liquid (Siemens) was used. As the reagent which contains the divalent-metal-ion-producing compound, aqueous solutions (2.5 mM) of salts of calcium, magnesium, zinc, and copper were each prepared as below.

*2.5 mM Calcium Chloride Aqueous Solution

The 25 mM calcium chloride liquid (Siemens) was diluted 10-fold with distilled water to obtain a 2.5 mM calcium chloride aqueous solution.

*2.5 mM Magnesium Chloride Aqueous Solution

First, magnesium chloride hexahydrate (Kishida Chemical Co., Ltd.) was dissolved in distilled water to prepare a 50 mM magnesium chloride aqueous solution. The obtained aqueous solution was diluted 20-fold with distilled water to obtain a 2.5 mM magnesium chloride aqueous solution.

*2.5 mM Copper Sulfate Aqueous Solution

First, copper (II) sulfate pentahydrate (Kishida Chemical Co., Ltd.) was dissolved in distilled water to prepare a 50 mM copper sulfate aqueous solution. The obtained aqueous solution was diluted 20-fold with distilled water, to obtain a 2.5 mM copper sulfate aqueous solution.

*2.5 mM Zinc Chloride Aqueous Solution

A 100 mM zinc chloride aqueous solution (Kishida Chemical Co., Ltd.) was diluted 40-fold with distilled water, to obtain a 2.5 mM zinc chloride aqueous solution.

(2) Blood Specimen

As the subject plasma, plasmas from LA positive patients (7 specimens), plasmas from coagulation factor VIII deficiency patients (4 specimens), plasmas from coagulation factor IX deficiency patients (4 specimens), and heparin-added plasmas (5 specimens) were used. As the normal plasma, Pooled Normal Plasma (Precision BioLogic Inc.) was used.

(3) Measurement of Clotting Time

Each specimen (50 µl) above was heated at 37° C. for 1 minute, and then, was mixed with the APTT reagent (50 µl), and the mixture was heated at 37° C. for 20 seconds. Then, the resultant mixture was mixed with the 2.5 mM aqueous solution (20 µl) of each metal salt above, to prepare a measurement sample. The final concentration of the divalent metal salt in each measurement sample was 0.416 mM. The obtained measurement sample was heated at 37° C. for about 3 minutes, then, the 25 mM calcium chloride liquid (50 µl) was added thereto, and then, clotting time was measured. As a control, measurement of clotting time by a conventional APTT measurement method was also conducted. That is, each specimen (50 µl) above was heated at 37° C. for 1 minute, and then, was mixed with the APTT reagent (50 µl), to prepare a measurement sample. The obtained measurement sample was heated at 37° C. for about 3 minutes, then, the 25 mM calcium chloride liquid (50 μl) was added thereto, and then, clotting time was measured. In Example 1, the measurement of clotting time was performed by a fully automatic clotting time measurement apparatus CS-2000i (Sysmex Corporation).

(4) Results

Figure 1:
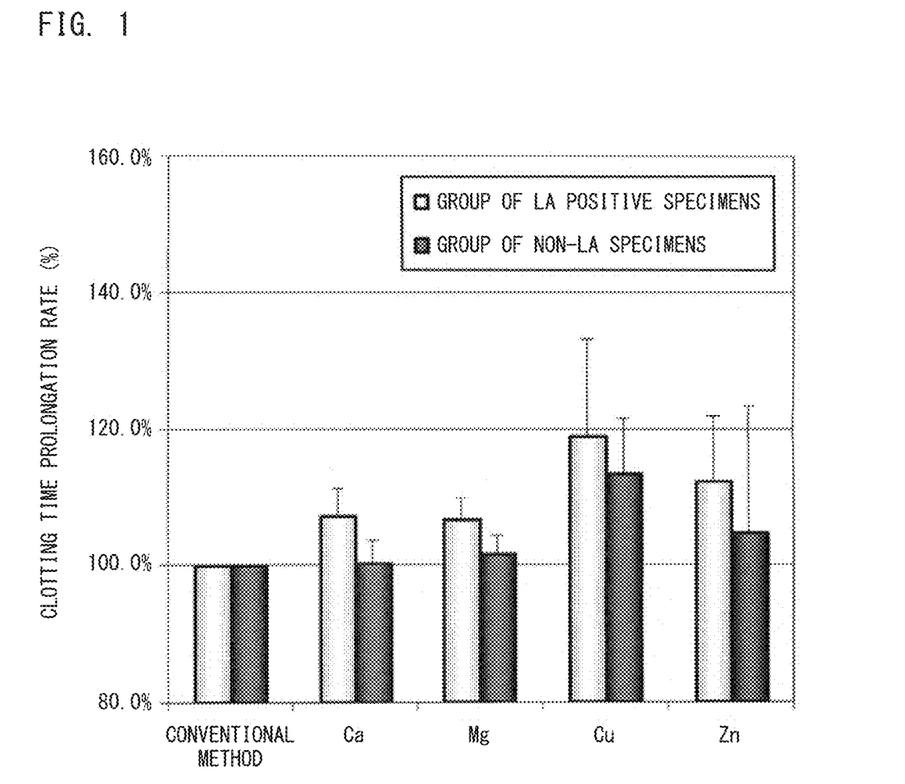
FIG. 1 is a graph showing a ratio (%) of the average value of the measured time obtained by a measurement method according to the present embodiment with respect to the average value of the measured time obtained by a conventional APTT measurement method.

The above blood specimens were divided into a group of LA positive specimens and a group of non-LA specimens (coagulation factor deficient specimens and heparin-added specimens). Then, for each group, the average of the measured time (seconds) was calculated. FIG. 1 shows the ratio of the average value of the measured time obtained from the measurement method according to the present embodiment with respect to the average value of the measured time of the control. In FIG. 1, the above ratio is expressed as prolongation rate (%), with the average value of the measured time of the control defined as 100%.

As shown in FIG. 1, it has been found that, with the measurement method according to the present embodiment, the clotting time of the group of LA positive specimens tends to be prolonged compared with the clotting time of the group of non-LA specimens. Thus, it is suggested that the measurement method according to the present embodiment has improved sensitivity to LA than that of the conventional measurement method.

Example 2

With respect to various types of blood specimens including LA positive specimens, clotting time was measured by the measurement method according to the present embodiment and by a conventional measurement method, and the ICA values were calculated from the measured clotting times and compared with one another.

(1) Reagent

In Example 2, the same reagents as those in Example 1 were used.

(2) Blood Specimen

In Example 2, the same subject plasmas and the same normal plasma as those in Example 1 were used. As the mixed plasma, each of the above subject plasmas and the normal plasma were mixed at 1:1, and the mixed plasmas in which the proportion of the subject plasma was 50% (v/v) were used.

(3) Measurement of Clotting Time and Calculation of Quantification Index (ICA)

Clotting time of each blood specimen was measured in the same manner as in Example 1 except that the mixed plasmas were added as blood specimens. As a control, measurement of clotting time by the conventional APTT measurement method was also conducted in the same manner as in Example 1. In accordance with the following formula, ICA of each specimen was calculated from clotting time.

$$ICA=[(b-c)/a]\times 100$$

(wherein, a: clotting time of subject plasma, b: clotting time of mixed plasma in which proportion of subject plasma is 50% (v/v), c: clotting time of normal plasma.)

(4) Results

Figure 2:
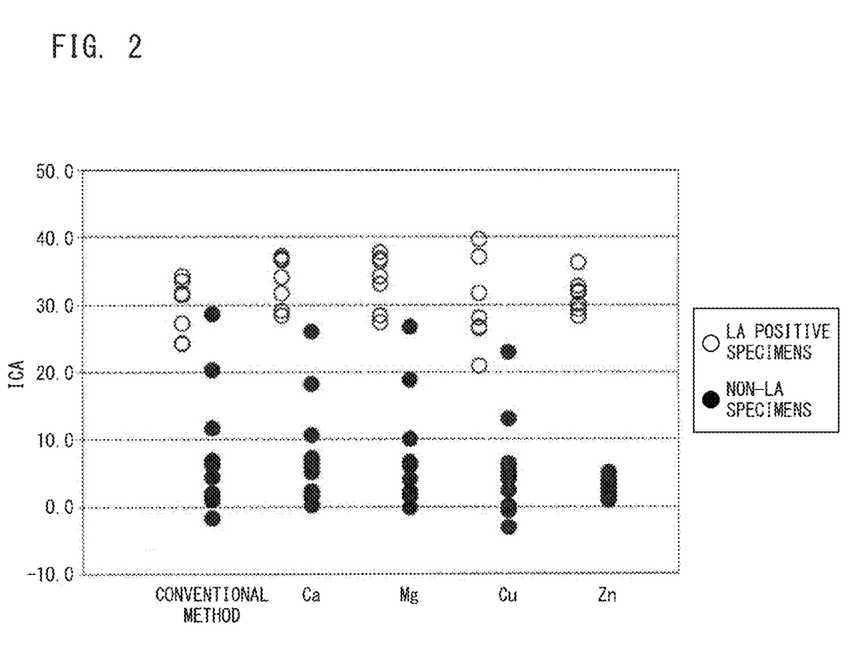
FIG. 2 is a distribution diagram on which, for each of a group of LA positive specimens and a group of non-LA specimens, values of Index of Circulating Anticoagulant (ICA) calculated from measured times obtained by a conventional APTT measurement method and by the measurement method according to the present embodiment are plotted.

The above blood specimens were divided into a group of LA positive specimens and a group of non-LA specimens (coagulation factor deficient specimens and heparin-added specimens), and then, a graph was created on which ICA of each specimen included in each group was plotted. FIG. 2 shows the created graph. In FIG. 2, each LA positive specimen is indicated by a white dot and each non-LA specimen is indicated by a black dot. As shown in FIG. 2, it is found that the measurement method according to the present embodiment can more clearly distinguish the group of LA positive specimens from the group of non-LA specimens, compared with the conventional measurement method.

What is claimed is:

1. A method for measuring clotting time comprising the sequential steps of:
   mixing a blood specimen suspected to contain a lupus anticoagulant and an activator selected from the group consisting of ellagic acid, kaolin, cerite, and silica to form a mixture; incubating the mixture at a predetermined temperature and for a predetermined time; preparing a measurement sample by mixing an amount of a divalent-metal-ion-producing compound for facilitating formation of a phospholipid-containing complex and the mixture of the blood specimen and the activator, wherein the amount of the divalent-metal-ion-producing compound is such that coagulation does not occur; and measuring a clotting time after adding, to the measurement sample, an aqueous solution of a calcium salt as a coagulation initiator, wherein the divalent-metal-ion-producing compound is at least one metal salt selected from the group consisting of calcium, magnesium, zinc and copper.

2. The method for measuring clotting time of claim 1, wherein a final concentration of the divalent-metal-ion-producing compound in the measurement sample is lower than a final concentration of the calcium salt added in the measuring of the clotting time.

3. The method for measuring clotting time of claim 1, wherein the divalent-metal-ion-producing compound is a salt composed of a divalent metal and an inorganic acid.

4. The method for measuring clotting time of claim 1, wherein in the measuring of the clotting time, the aqueous solution of the calcium salt is added after the measurement sample is incubated under a predetermined condition.

5. The method for measuring clotting time of claim 4, wherein the predetermined condition is a condition of performing the incubation at a temperature of not lower than 35° C. and not higher than 40° C., for a time period of not shorter than 2 minutes and not longer than 5 minutes.

6. The method for measuring clotting time of claim 1, wherein a phospholipid is further mixed in the preparing of the measurement sample.

7. The method for measuring clotting time of claim 1, wherein at least one selected from a subject plasma, and a mixed plasma composed of a subject plasma and a normal plasma is used as the blood specimen.

8. The method for measuring clotting time of claim 1, wherein a clotting time of a normal plasma is further measured after adding an aqueous solution of a calcium salt as a coagulation initiator.

9. The method for measuring clotting time of claim 1, wherein the phospholipid-containing complex comprises at least phospholipids and divalent metal ions.

10. The method for measuring clotting time of claim 9, wherein the phospholipid-containing complex further comprises proteins.

11. A method for determining presence or absence of a lupus anticoagulant, the method comprising the sequential steps of:
   mixing a blood specimen and an activator selected from the group consisting of ellagic acid, kaolin, cerite, and silica to form a mixture;

incubating the mixture at a predetermined temperature and for a predetermined time; preparing a measurement sample by mixing an amount of a divalent-metal-ion-producing compound for facilitating formation of a phospholipid-containing complex and the mixture of the blood specimen and the activator, wherein the amount of the divalent-metal-ion-producing compound is such that coagulation does not occur; and measuring a clotting time after adding, to the measurement sample, an aqueous solution of a calcium salt as a coagulation initiator, and determining whether the blood specimen contains a lupus anticoagulant on the basis of the clotting time, wherein the divalent-metal-ion-producing compound is at least one metal salt selected from the group consisting of calcium, magnesium, zinc and copper.

12. The method for determining presence or absence of a lupus anticoagulant of claim 11, wherein in the determining, a quantification index is obtained on the basis of the measured clotting time, and whether the blood specimen contains a lupus anticoagulant is determined on the basis of a value of the obtained quantification index.

13. The method for determining presence or absence of a lupus anticoagulant of claim 12, wherein
in the determining, the value of the quantification index is compared with a predetermined threshold value,
when the value of the quantification index is greater than or equal to the predetermined threshold value, it is determined that the blood specimen contains a lupus anticoagulant, and
when the value of the quantification index is smaller than the predetermined threshold value, it is determined that the blood specimen does not contain a lupus anticoagulant.

14. The method for determining presence or absence of a lupus anticoagulant of claim 12, wherein the quantification index is Index of Circulating Anticoagulant (ICA), Percent Correction (PC), or Response Curve-Score (RC-S).

15. The method for determining presence or absence of a lupus anticoagulant of claim 11, wherein the phospholipid-containing complex comprises at least phospholipids and divalent metal ions.

16. The method for determining presence or absence of a lupus anticoagulant of claim 15, wherein the phospholipid-containing complex further comprises proteins.

17. A reagent kit for detecting a lupus anticoagulant comprising:
a first reagent that contains a divalent-metal-ion-producing compound for facilitating formation of a phospholipid-containing complex;
a second reagent that contains an activator selected from the group consisting of ellagic acid, kaolin, cerite, and silica; and
a coagulation initiation reagent composed of an aqueous solution of a calcium salt,
wherein the divalent-metal-ion-producing compound is at least one metal salt selected from the group consisting of calcium, magnesium, zinc and copper, and
a concentration of a divalent-metal-ion-producing compound in the first reagent is not lower than 1.0 mM and not higher than 10 mM.

18. The reagent kit for detecting a lupus anticoagulant of claim 17, wherein at least one of the first reagent and the second reagent further contains a phospholipid.

19. The reagent kit for detecting a lupus anticoagulant of claim 17, wherein the divalent-metal-ion-producing compound is a salt composed of a divalent metal and an inorganic acid.

20. The reagent kit for detecting a lupus anticoagulant of claim 17, wherein a concentration of the aqueous solution of a calcium salt is not lower than 2.5 mM and not higher than 40 mM.

* * * * *